United States Patent
Varming et al.

(10) Patent No.: US 6,727,260 B2
(45) Date of Patent: Apr. 27, 2004

(54) INHIBITORS OF PROTON-GATED CATION CHANNELS AND THEIR USE IN THE TREATMENT OF ISCHAEMIC DISORDERS

(75) Inventors: Thomas Varming, Charlottenlund (DK); Frank Wätjen, Farum (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 09/985,887

(22) Filed: Nov. 6, 2001

(65) Prior Publication Data

US 2002/0058663 A1 May 16, 2002

Related U.S. Application Data

(63) Continuation of application No. PCT/DK00/00257, filed on May 12, 2000.

(30) Foreign Application Priority Data

May 19, 1999 (DK) ........................................ 1999-00695

(51) Int. Cl.$^7$ .................. A61K 31/4745; C07D 471/02
(52) U.S. Cl. .......................... 514/292; 546/84; 514/290
(58) Field of Search ................................. 514/292, 290; 546/84

(56) References Cited

U.S. PATENT DOCUMENTS 5,436,250 A * 7/1995 Watjen et al. ............... 514/292

FOREIGN PATENT DOCUMENTS

| EP | 0 432 648 B1 | 6/1991 |
|---|---|---|
| EP | 0 522 494 B1 | 1/1993 |
| EP | 0 633 262 A1 | 1/1995 |
| WO | WO 93/05043 | 3/1993 |
| WO | WO 94/26747 | 11/1994 |
| WO | WO 96/08494 | 3/1996 |
| WO | WO 96/08495 | 3/1996 |
| WO | WO 98/14447 | 4/1998 |
| WO | WO 98/35034 | 8/1998 |
| WO | WO 99/11784 | 3/1999 |
| WO | WO 99/21981 | 5/1999 |
| WO | WO 00/08149 | 2/2000 |
| WO | WO 00/43514 | 7/2000 |

OTHER PUBLICATIONS

Waldmann, Rainer et al., Nature, vol. 386, Mar. 13, 1997; pp.173–177.
Barbry, Pascal et al., American Journal of Physiology, vol. 273, pp. G571–G585; 1997.
Lingueglia, Eric et al., The Journal of Biological Chemistry; vol. 272, No. 47, Issue of Nov. 21, 1997; pp. 29778–29783.
Bassilana, Frederic et al., The Journal of Biological Chemistry; vol. 272, No. 46, issue of Nov. 14, 1997, pp. 28819–28822.
Olson, Timothy H. et al., NeuroReport, vol. 9, pp. 1109–1113 (1998).
Chen, Chih–Cheng et al., Proc. Natl. Acad. Sci. USA, vol. 95, pp. 10240–10245, 1998.
Coscoy, Sylvie et al., The Journal of Biological Chemistry, Vol 274, No. 15, Issue of Apr. 9, 1999, pp. 10129–10132.
Varming, Thomas, Neuropharmacology, vol. 38, 1999, pp. 1875–1881.

* cited by examiner

Primary Examiner—Charanjit S. Aulakh
(74) Attorney, Agent, or Firm—Birch, Stewart, Kolasch & Birch, LLP

(57) ABSTRACT

This invention relates to the use of compounds capable of inhibiting the activity of a proton-gated cation channel in the treatment of alleviation of diseases or disorders associated with, or mediated by a drop in extra cellular pH.

16 Claims, 7 Drawing Sheets

INHIBITORS OF PROTON-GATED CATION CHANNELS AND THEIR USE IN THE TREATMENT OF ISCHAEMIC DISORDERS

This is a continuation of PCT Application No. PCT/DK00/00257, filed May 12, 2000.

TECHNICAL FIELD

This invention relates to the use of compounds capable of inhibiting the activity of a proton-gated cation channel in the treatment or alleviation of diseases or disorders associated with, or mediated by a drop in extracellular pH.

BACKGROUND ART

For almost 20 years, proton-gated cation channels have been known to exist in membranes of sensory neurons, where they are assumed to participate in nociception. Recently, several Acid Sensing Ion Channels (ASIC) have been cloned, and while some of these like ASIC3 (DRASIC) and ASIC-β are selectively expressed in sensory ganglia and/or the spinal cord, others, like ASIC1 and ASIC2, are expressed also in the brain [see e.g. Waldmann R, Champigny G, Bassilana F, Heurteaux C, Lazdunski M: A proton-gated cation channel involved in acid-sensing; *Nature* 1997 386 (6621)173–177; Lingueglia E, De Weille J R, Bassilana F, Heurteaux C, Sakai H, Waldmann R, Lazdunski M: A modulatory subunit of acid sensing ion channels in brain and dorsal root ganglion cells; *J. Biol. Chem.* 1997 272 (47) 29778–29783; Bassilana F, Champigny G, Waldmann R, De Weille J R, Heurteaux C, Lazdunski M: The acid-sensitive ionic channel subunit ASIC and the mammalian degenerin MDEG form a heteromultimeric H+-gated Na+ channel with novel properties; *J. Biol. Chem.* 1997 272 (46) 28819–28822; Olson T H, Riedl M S, Vulchanova L, Ortiz-Gonzalez X R, Elde R: An acid sensing ion channel (ASIC) localizes to small primary afferent neurons in rats; NeuroReport 1998 9 (6) 1109–1113; Chen C -C, England S, Akopian A N, Wood J N: A sensory neuron-specific, proton-gated ion channel; *Proc. Natl. Acad. Sci. USA* 1998 95 (17) 10240–10245; and Coscoy S, de Weille J R, Lingueglia E, Lazdunski M: The pre-transmembrane 1 domain of acid—sensing ion channels participates in the ion pore; *J. Biol. Chem.* 1997 274 (15) 10129–101321].

The proton-gated channels cloned all belong to the amiloride-sensitive Na-channel/degenerin family of ion channels, and like for ionotropic purinergic receptors, the topology presumably is two transmembrane domains flanking a long extracellular loop.

Compounds inhibiting the proton-gated cation channels have been suggested useful for the treatment of pain.

WO 98/35034 discloses mammal neuronal acid sensing cationic channels, which are considered useful for screening for analgesic drugs and for the treatment of degeneration of periferic neurons Since the demonstration that the level of extracellular glutamate in the brain is greatly elevated under ischaemia, much pharmaceutical research has been focused on design of glutamate receptor antagonists. There has, however, been discrepancy between in vitro and in vivo studies: especially with respect to the effect of antagonists of the N-methyl-D-aspartate (NMDA) subtype of glutamate receptors. In vitro, neuro degeneration due to oxygen/glucose deprivation is blocked by the NMDA receptor antagonist MK-801, but not by α-amino-3-hydoxy-5-methyl4-isoxazolepropionic acid (AMPA) receptor antagonists. Strikingly, the case is opposite in in vivo models of global cerebral ischaemia: AMPA receptor antagonists reduces infarct volume, while NMDA receptor antagonists are ineffective.

Isatin derivatives like those described herein, for use as AMPA antagonists have been disclosed in e.g. WO 94/26747, WO 96/08494 and WO 96/08495. However, the use of these isatin derivatives as ASIC antagonising compounds have never been disclosed.

SUMMARY OF THE INVENTION

The present work shows the presence of ASIC in cultured mouse cortical neurons, a preparation widely used for studying native ion channels and in vitro models of neuro degeneration after ischaemia.

The presence of ASIC in central neurons is of particular interest because tissue acidosis is a well established feature of cerebral ischaemia. While the acidic pH in general has been regarded as neuro-protective due to proton inhibition of NMDA receptors, it may also have adverse effects by reason of activation of acid sensing ion channels contributing to membrane depolarisation, subsequent $Ca^{2+}$ accumulation and neuro-degeneration.

Therefore, in a first aspect, the invention relates to the use of a compound capable of inhibiting a mammalian proton-gated cation channel for the manufacture of a medicament for the treatment, prevention or alleviation of a disease, disorder or condition associated with, or mediated by a drop in extracellular pH.

In another aspect the invention provides a method for the treatment, prevention or alleviation of a disease, disorder or condition in a subject, including a human, which disease, disorder or condition is associated with, or mediated by a drop in extracellular pH, said method comprising administering to the subject a pharmaceutically effective amount of a compound capable of inhibiting a mammalian proton-gated cation channel.

Other objects of the invention will be apparent to the person skilled in the art from the following detailed description and the examples.

DETAILED DISCLOSURE OF THE INVENTION

ASIC Antagonising Compounds

In its first aspect the invention relates to the use of compounds capable of inhibiting a mammalian proton-gated cation channels for the manufacture of medicaments for the treatment, prevention or alleviation of a disease, disorder or condition associated with, or mediated by a drop in extracellular pH.

In the context of this invention compounds capable of inhibiting a mammalian proton-gated cation channel is also designated ASIC antagonising compounds.

Method of Screening

The ASIC antagonising compounds of the invention may be identified using the following screening method, which method comprises the subsequent steps of (i) subjecting a proton-gated cation channel containing cell to the action of protons by adjustment of the pH to an acidic level;

(ii) subjecting a proton-gated cation channel containing cell to the action of the chemical compound; and (iii) monitoring the change in membrane potential or the current induced by protons on the proton-gated cation channel containing cell.

In a preferred embodiment, the proton-gated cation channel is ASIC1 (also known as human brain sodium channel channel 2 (hBNaC2)), ASIC1A, ASIC1B, ASIC2 (also known as human brain sodium channel channel 1 (hBNaC1), or MDEG1), ASIC2A, ASIC2B, ASIC3 (also known as DRASIC), or ASIC-β.

The proton-gated cation channel may or may not be endogenous to the cell in question, i.e. be a channel naturally occurring in the cell.

Cells for use in the method of the invention, in which proton-gated cation channel are naturally present includes cortical neuronal cells, in particular mouse or rat cortical neuronal cells, and human embryonic kidney (HEK) cells, in particular HEK 293 cells.

Alternatively the proton-gated cation channel may be exogenous to the cell in question, and may in particular be introduced by recombinant DNA technology, such as transfection or infection. Such cells include Chinese hamster ovary (CHO) cells, *Xenopus laevis* oocytes, or any other cell lines capable to express proton-gated cation channels.

The proton-gated cation channel containing cells may be subjected to the action of protons by adjustment of the pH to an acidic level using any convenient acid or buffer, including organic acids such as formic acid, acetic acid, citric acid, ascorbic acid and lactic acid, and inorganic acids such as hydrochloric acid, hydrobromic acid and nitric acid, perchloric acid and phosphoric acid.

In the method of the invention, the current flux induced by protons over the membrane of the proton-gated cation channel containing cell may be monitored by patch clamp techniques.

Alternatively, the change in membrane potential induced by protons of the proton-gated cation channel containing cells may be monitored using fluorescence methods. When using fluorescence methods, the proton-gated cation channel containing cells are incubated with a membrane potential indicating agent, that allow for a determination of changes in the membrane potential of the cells, caused by the added protons. Such membrane potential indicating agents include fluorescent indicators, preferably $DIBAC_4(3)$, $DiOC5(3)$, and $DiOC2(3)$.

In a preferred embodiment, the change in membrane potential induced by protons on the proton-gated cation channel containing cells are monitored by spectroscopic methods, e.g. using a FLIPR assay (Fluorescence Image Plate Reader; available from Molecular Devices).

The ASIC antagonising compounds of the invention show activity in concentrations below 100 μM, preferably below 10 μM, more preferred below 1 μm. In its most preferred embodiment the ASIC antagonising compounds show activity in low micromolar and the nanomolar range.

Preferred ASIC Antagonising Compounds

In a preferred embodiment the compound for use according to the present invention is an isatin derivative represented by the general Formula I

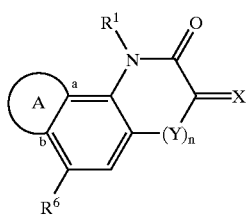

(I)

or a pharmaceutically acceptable salt thereof, wherein $R^1$ represents hydrogen, alkyl, phenyl or benzyl; and X represents oxygen, or a group of the formula $NOR^2$ (i.e. an oxim), wherein $R^2$ represents hydrogen, alkyl, acyl, phenyl or benzyl; and Y represents a group of the formula $N-R^4$, wherein $R^4$ represents hydrogen, hydroxy or alkyl; and n is 0 or 1; and $R^6$ represents phenyl, naphthyl, thienyl, or pyridyl, all of which groups may be substituted one or more times with halogen, $CF_3$, nitro, amino, cyano, hydroxy alkyl, alkoxy or phenyl, or a group of the formula $—SO_2NR'R''$, wherein NR' and R'' independently of each another represents hydrogen or alkyl; and "A" represents a ring holding of from five to seven atoms, which ring is fused to the benzo-ring at the positions marked "a" and "b", and formed by one or the following bivalent radicals:

(a) $—CH_2—CH_2—CH_2—$ (b),
(a) $—NR^{12}—CH_2—CH_2—$ (b),
(a) $—CH_2—NR^{12}—CH_2—$ (b),
(a) $—CH_2—CH_2—NR^{12}—$ (b),
(a) $—CH_2—CH_2—CH_2—CH_2—$ (b),
(a) $—NR^{12}—CH_2—CH_2—CH_2—$ (b),
(a) $—CH_2—NR^{12}—CH_2—CH_2—$ (b),
(a) $—CH_2—CH_2—NR^{12}—CH_2—$ (b),
(a) $—CH_2—CH_2—CH_2—NR^{12}—$ (b),
(a) $—CH_2—CH_2—CH_2—CH_2—CH_2—$ (b),
(a) $—NR^{12}—CH_2—CH_2—CH_2—CH_2—$ (b),
(a) $—CH_2—NR^{12}—CH_2—CH_2—CH_2—$ (b),
(a) $—CH_2—CH_2—NR^{12}—CH_2—CH_2—$ (b),
(a) $—CH_2—CH_2—CH_2—NR^{12}—CH_2—$ (b), or
(a) $—CH_2—CH_2—CH_2—CH_2—NR^{12}—$ (b), wherein $R^{12}$ represents hydrogen, alkyl, alkyl substituted with hydroxy, alkoxy-alkyl, alkoxy-carbonyl-alkyl, alkyl-carbonyl-oxy-alkyl, cycloalkyl, cycloalkyl-alkyl, alkenyl, alkynyl, phenyl or benzyl, which phenyl or benzyl group is optionally substituted with halogen, $CF_3$, nitro, amino, cyano, hydroxy alkyl, alkoxy, or a group of the formula $—SO_2NR'R''$, wherein R' and R'' independently of each another represents hydrogen or alkyl.

In another preferred embodiment, the compound for use according to the present invention is represented by the general Formula II

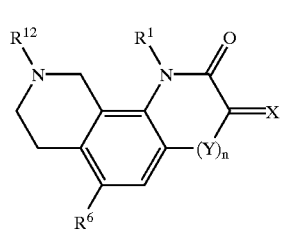

(II)

or a pharmaceutically acceptable salt thereof, wherein $R^1$, $R^6$, $R^{12}$, X, Y and n have the meanings set forth above.

In a third preferred embodiment, the compound for use according to the present invention is represented by the general Formula III

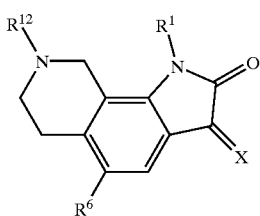

(III)

or a pharmaceutically acceptable salt thereof, wherein $R^1$, $R^6$, $R^{12}$ and X have the meanings set forth above.

In a more preferred embodiment, the compound represented by Formula III is 8-ethyl-5-phenyl-6-7-8-9-tetrahydro-1H-pyrrolo-[3,2-h]-isoquinoline-2,3-dione-3-oxim;

8-methyl-5-phenyl-6-7-8-9-tetrahydro-1H-pyrrolo-[3,2-h]-isoquinoline-2,3-dione-3-oxim;

8-methyl-5-phenyl-6-7-8-9-tetrahydro-1H-pyrrolo-[3,2-h]-isoquinoline-2,3-dione-3-methyloxim;

5-phenyl-6-7-8-9-tetrahydro-1H-pyrrolo-[3,2-h]-isoquinoline-2,3-dione-3-oxim;

5-(4-chlorophenyl)-8-methyl-6-7-8-9-tetrahydro-1-H-pyrrolo-[3,2-h]-isoquinoline-2,3-dione-3-oxim;

5-(2-naphthyl)-8-methyl-6-7-8-9-tetrahydro-1-H-pyrrolo-[3,2-h]-isoquinoline-2,3-dione-3-oxim;

8-methyl-5-phenyl-6,7,8,9-tetrahydro-1H-pyrrolo-[3,2-h]-isoquinoline-2,3-dione-3-acetyloxim;

8-methyl-5-(4-(N,N-dimethylsulfamoyl)-phenyl)-6,7,8,9-tetrahydro-1H-pyrrolo-[3,2-h]-isoquinoline-2,3-dione-3-oxime;

8-benzyl-5-Phenyl-6-7-8-9-tetrahydro-1H-pyrrolo-[3,2-h]-isoquinoline-2,3-dione-3-oxim;

8-methoxycarbonylmethyl-5-phenyl-6,7,8,9-tetrahydro-1H-pyrrolo-[3,2-h]-isoquinoline-2,3-dione-3-oxime;

8-(2-propynyl)-5-phenyl-6,7,8,9-tetrahydro-1H-pyrrolo-[3,2-h]-isoquinoline-2,3-dione-3-oxime; or 8-cyclopropylmethyl-5-phenyl-6,7,8,9-tetrahydro-1H-pyrrolo-[3,2-h]-isoquinoline-2,3-dione-3-oxime;

or a pharmaceutically acceptable salt thereof.

In a fourth preferred embodiment, the compound for use according to the present invention is represented by the general Formula IV

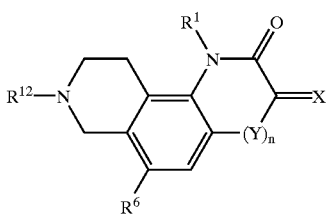

(IV)

or a pharmaceutically acceptable salt thereof, wherein $R^1$, $R^6$, $R^{12}$, X, Y and n have the meanings set forth above.

In a fifth preferred embodiment, the compound for use according to the present invention is represented by the general Formula V

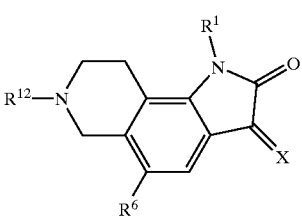

(V)

or a pharmaceutically acceptable salt thereof, wherein $R^1$, $R^6$, $R^{12}$ and X have the meanings set forth above.

In a sixth preferred embodiment, the compound for use according to the present invention is represented by the general Formula VI

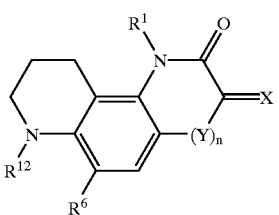

(VI)

or a pharmaceutically acceptable salt thereof, wherein $R^1$, $R^6$, $R^{12}$, X, Y and n have the meanings set forth above.

In a seventh preferred embodiment, the compound for use according to the present invention is represented by the general Formula VII

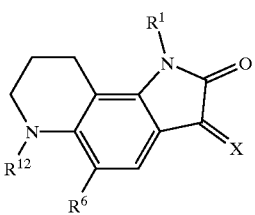

(VII)

or a pharmaceutically acceptable salt thereof, wherein $R^1$, $R^6$, $R^{12}$ and X have the meanings set forth above.

In a more preferred embodiment, the compound represented by Formula VII is 7-ethyl-5-phenyl-6,7,8,9-tetrahydro-1H-pyrrolo-[3,2-f]-isoquinoline-2,3-dione-3-oxim; or 5-phenyl-7-methyl-6-7-8-9-tetrahydro-1-methyl-pyrrolo-[3,2-f]-isoquinoline-2,3-dione-3-oxim;

or a pharmaceutically acceptable salt thereof.

In an eight preferred embodiment, the compound for use according to the present invention is represented by the general Formula VIII

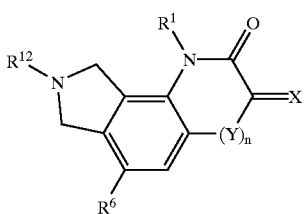

(VIII)

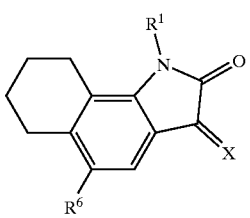

(XI)

or a pharmaceutically acceptable salt thereof, wherein $R^1$, $R^6$, $R^{12}$, X, Y and n have the meanings set forth above.

In a ninth preferred embodiment, the compound for use according to the present invention is represented by the general Formula IX

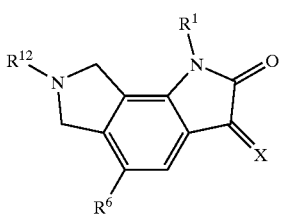

(IX)

or a pharmaceutically acceptable salt thereof, wherein $R^1$, $R^6$, $R^{12}$ and X have the meanings set forth above.

In a more preferred embodiment, the compound represented by Formula IX is 7-methyl-5-phenyl-1-6-7-8-tetrahydrobenzo-[2,1-b:3,4-c]-dipyrrole-2,3-dione-3-oxime;

7-methyl-5-(1-naphthyl)-1-6-7-8-tetrahydrobenzo-[2,1-b:3,4-c]-dipyrrole-2,3-dione-3-oxime; or 7-ethyl-5-phenyl-1-6-7-8-tetrahydrobenzo-[2,1-b:3,4-c]-dipyrrole-2,3-dione-3-oxime;

or a pharmaceutically acceptable salt thereof.

In a tenth preferred embodiment, the compound for use according to the present invention is represented by the general Formula X

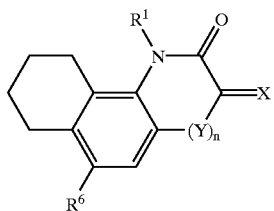

(X)

or a pharmaceutically acceptable salt thereof, wherein $R^1$, $R^6$, X, Y and n have the meanings set forth above.

In an eleventh preferred embodiment, the compound for use according to the present invention is represented by the general Formula XI or a pharmaceutically acceptable salt thereof, wherein $R^1$, $R^6$, and X have the meanings set forth above.

In a more preferred embodiment, the compound represented by Formula XI is 5-phenyl-6-7-8-9-tetrahydro-1-H-pyrrolo-[3,2-h]-naphthalene-2,3-dione-3-oxim; or 5-(4-chlorophenyl)-6-7-8-9-tetrahydro-1-H-pyrrolo-[3,2-h]-naphthalene-2,3-dione-3-oxim;

or a pharmaceutically acceptable salt thereof.

In a twelfth preferred embodiment, the compound for use according to the present invention is represented by the general Formula XII

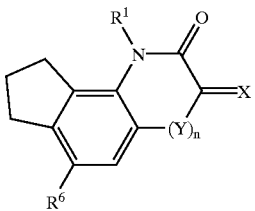

(XII)

or a pharmaceutically acceptable salt thereof, wherein $R^1$, $R^6$, X, Y and n have the meanings set forth above.

In a thirteenth preferred embodiment, the compound for use according to the present invention is represented by the general Formula XIII

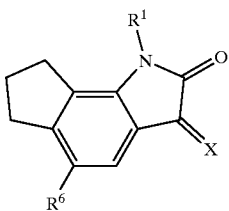

(XIII)

or a pharmaceutically acceptable salt thereof, wherein $R^1$, $R^6$, and X have the meanings set forth above.

In a fourteenth preferred embodiment, the compound for use according to the present invention is N-amidino-3,5-diamino-6-chloropyrazine-2-carboxamide (Amiloride).

Definition of Substituents

In the context of this invention halogen represents a fluorine, a chlorine, a bromine or an iodine atom. Thus, a trihalogenmethyl group represents e.g. a trifluoromethyl group and a trichloromethyl group.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention an alkenyl group designates a carbon chain containing one or more double bonds, including di-enes, tri-enes and poly-enes. In a preferred embodiment the alkenyl group of the invention comprises of from two to eight carbon atoms ($C_{2-8}$-alkenyl), more preferred of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, or 1,3-butenyl; 1-, 2-, 3-, 4- or 5-hexenyl, or 1,3-hexenyl, or 1,3,5-hexenyl; 1-, 2-, 3-, 4-, 5-, 6-, or 7-octenyl, or 1,3-octenyl, or 1,3,5-octenyl, or 1,3,5,7-octenyl.

In the context of this invention an alkynyl group designates a carbon chain containing one or more triple bonds, including di-ynes, tri-ynes and poly-ynes. In a preferred embodiment the alkynyl group of the invention comprises of from two to eight carbon atoms ($C_{2-8}$-alkynyl), more preferred of from two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, or 1,3-butynyl; 1-, 2-, 3-, 4-pentynyl, or 1,3-pentynyl; 1-, 2-, 3-, 4-, or 5-henynyl, or 1,3,5-hexynyl or 1,3,5-hexynyl; 1-, 2-, 3-, 4-, 5- or 6-heptynyl, or 1,3-heptynyl, or 1,3,5-heptynyl; 1-, 2-, 3-, 4-, 5-, 6- or 7-octynyl, or 1,3-octynyl, or 1,3,5-octynyl, or 1,3,5,7-octynyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above.

In the context of this invention an alkoxy-alkyl group designates an "alkyl-O-alkyl-" group, wherein alkyl is as defined above.

In the context of this invention an acyl group designates a carboxy group (—COOH) or an alkyl-carbonyl group (alkyl-CO—), wherein alkyl is as defined above. Examples of preferred acyl groups of the invention include carboxy, acetyl, and propionyl.

In the context of this invention an alkoxy-carbonyl-alkyl group designates an "alkyl-O—CO-alkyl" group, wherein alkyl is as defined above.

In the context of this invention an alkyl-carbonyl-oxy-alkyl group designates an "alkyl-CO—O-alkyl-" group, wherein alkyl is as defined above.

In the context of this invention an amino group may be a primary (—$NH_2$), secondary (—NH-alkyl), or tertiary (—N(alkyl)$_2$) amino group, i.e. it may be substituted once or twice with an alkyl group as defined above.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

Metal salts of a chemical compound of the invention includes alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

The chemical compound of the invention may be provided in dissoluble or indissoluble forms together with a pharmaceutically acceptable solvents such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in *"Enantiomers, Racemates, and Resolutions"*, John Wiley and Sons, New York (1981).

Optical active compounds can also be prepared from optical active starting materials.

Moreover, some of the chemical compounds of the invention being oximes, may thus exist in two forms, syn- and anti-form (Z- and E-form), depending on the arrangement of the substituents around the —C=N— double bond. A chemical compound of the present invention may thus be the syn- or the anti-form (Z- and E-form), or it may be a mixture hereof.

Methods of Preparation

The chemical compounds of the invention may be prepared by conventional methods for chemical synthesis, e.g. those described in WO 94/26747, WO 96108494 and WO 96108495, and in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The presence of ASIC in central neurons is of particular interest because tissue acidosis is a well established feature of cerebral ischaemia. While the acidic pH in general has been regarded as neuro-protective, due to proton inhibition of NMDA receptors, it may also have adverse effects by reason of activation of acid sensing ion channels contributing to membrane depolarisation, subsequent $Ca^{2+}$ accumulation and neuro-degeneration. In this respect it seems justified that the administration of ASIC antagonising compounds provide protection to individuals against injury arising from a drop in extracellular pH.

Diseases and disorders contemplated according to the present invention include in particular diseases of the central nervous system (CNS). In particular, the invention relates to combating diseases associated with reduced blood flow to the brain and other CNS tissue and with instances of a temporary break in blood supply to the brain or to other CNS tissue. Examples include ischaemic diseases, anoxic episodes, and injury to the brain and other parts of the CNS caused by trauma or other injury, for example a blow to the head, or spinal injury. In such reduced blood flow episodes, or episodes where there is a temporary break in blood supply, oxygen supply to the brain is reduced or interrupted.

Diseases and disorders contemplated according to the present invention also include cerebrovascular disorders such as cerebral ischaemia or cerebral infarction resulting from a range of conditions, such as tromboembolic or haemorrhagic stroke, cerebral vasospasm, hypoglycaemia, cardiac arrest, status epilepticus, perinatal asphyxia, anoxia such as from near-drowning, pulmonary surgery and cerebral trauma as well as lathyrism, Alzheimer's disease, and Huntington's disease. The method can be used in the treatment or prevention of traumatic brain injury, in particular ischaemic, hypoxic or anoxic brain damage, spinal cord injury, tissue ischaemia and reperfusion injury in a mammal at risk for such damage.

The brain damage may follow cerebral ischaemia, either global or focal, or be caused by cardiac arrest, or may follow high risk surgery such as cardiac surgery. It may also follow or be caused by stroke, neonatal hypoxia, hypoxia caused by compromised lung function, neonatal anoxia, anoxia caused by compromised lung function, cerebral trauma, secondary regional ischaemia induced by brain oedema, increased intercranial pressure, open brain surgery, endarterectomy, surgical interventions involving temporary, artificially sustained arrest of cardiopulmonary functions resulting in impairment of cerebral blood flow, and emergency treatment involving cardiopulmonary resuscitation (CPR).

As used herein, reperfusion injury refers to the cellular changes and tissue damage seen after a period of total ischaemia followed by reperfusion. Extremity re-plantation, organ transplantation, free flap tissue reconstruction and even myocardial infarction and stroke are all clinical examples of interval tissue ischaemia which can lead to tissue loss due to reperfusion injury after blood flow is re-established. Tissue reperfusion injury, seen in its full clinical extent as the no-reflow phenomenon, appears as inflammatory response to reperfusion resulting in the ultimate death of the tissue.

Thus the chemical compounds of the invention are found to be particularly useful in acute treatment of ischaemic stroke, in treatment of brain damage following global cerebral ischaemia, or for prevention of brain damage following high risk surgery.

In many instances of brain ischaemia, treatment is not available to the patient for several, e.g. up to 6 hours, in stroke patients typically 3 to 6 hours, after the ischaemic injury. Such a delay places great demands on any therapeutic regime designed to mitigate ischaemic brain injury.

When administered post-ischaemically it is advisable that the chemical compounds of the invention be administered within one day of the ischaemic insult. Although the neuro-protective agent used in the invention may be administered as late as 14 hours after brain reperfusion, the treatment should preferably be carried out within 12 hours of ischaemic alleviation or reperfusion. Preferably, the treatment should occur within 6 hours of alleviation of ischaemia. Yet more preferred is the administration of the chemical compounds used in the invention within 3 hours of alleviation of ischaemia.

Pharmaceutical Compositions

Thus viewed from one aspect, the invention provides ASIC antagonising compounds for use in the manufacture of a pharmaceutical composition for treatment or alleviation of diseases and disorders associated with or mediated by a drop in extracellular pH.

In a preferred embodiment of this aspect, pharmaceutical compositions for treatment or alleviation of diseases and disorders associated with or mediated by a drop in extracellular pH, which pharmaceutical compositions comprise a pharmaceutically effective amount of an ASIC antagonising compound together with a pharmaceutically effective amount of an AMPA receptor antagonising compound.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising an ASIC antagonising compound or a pharmaceutically acceptable salt or derivative thereof, together with one or more pharmaceutically acceptable carriers therefor, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route which suite the desired therapy. Preferred routes of administration include oral administration, in particular in tablet, in capsule, in drage, in powder, or in liquid form, and parenteral administration, in particular cutaneous, subcutaneous, intramuscular, or intravenous injection. The pharmaceutical composition may be prepared by the skilled person using standard and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 $\mu$g/kg i.v. and 1 $\mu$g/kg p.o. The upper limit of the dosage range is presently considered to be about 10 mg/kg i.v. and 100 mg/kg p.o. Preferred ranges are from about 0.1 $\mu$g/kg to about 10 mg/kg/day i.v., and from about 1 $\mu$g/kg to about 100 mg/kg/day p.o.

Methods of Therapy

Viewed from another aspect, the invention provides a method for treatment, prevention or alleviation of a disease or a disorder or a condition of a living animal body, including a human, which disease or a disorder or a condition is associated with, or mediated by a drop in extracellular pH, said method comprising administering to a subject a pharmaceutically effective amount of a proton-gated cation channel inhibiting compound.

In a preferred embodiment, the disease, disorder or condition is associated with reduced blood flow to the brain and other CNS tissue, or associated with instances of a temporary break in blood supply to the brain or to other CNS tissue.

In another preferred embodiment, the disease, disorder or condition is an ischaemic disease, an anoxic episode, an injury to the brain and other parts of the CNS caused by trauma or other injury, a blow to the head, or a spinal injury, a tromboembolic or haemorrhagic stroke, a cerebral vasospasm, hypoglycaemia, cardiac arrest, status epilepticus, perinatal asphyxia, anoxia, cerebral trauma, lathyrism, Alzheimer's disease, and Huntington's disease, cerebral ischaemia or cerebral infarction, ischaemic, hypoxic or anoxic brain damage, spinal cord injury, tissue ischaemia and reperfusion injury in a mammal at risk for such damage.

In a third preferred embodiment of this aspect, the method of the invention comprises co-administration of an ASIC antagonising compound and a pharmaceutically effective amount of an AMPA receptor antagonising compound.

In a more preferred embodiment, the AMPA receptor antagonising compound is 2,3-dihydroxy-6-nitro-7-sulphamoyl-benzo-(f)-quinoxaline (NBQX), 6,7-dinitroquinoxaline-2,3-dione, or 6-cyano-7-nitroquinoxaline-2,3-dione, or a pharmaceutically acceptable salt thereof.

It is at present contemplated that suitable dosage ranges are 0.1 to 1000 milligrams daily, 10–500 milligrams daily, and especially 30–100 milligrams daily, dependent as usual upon the exact mode of administration, form in which administered, the indication toward which the administration is directed, the subject involved and the body weight of the subject involved, and further the preference and experience of the physician or veterinarian in charge.

AMPA Receptor Antagonists

AMPA receptor antagonising compounds are well known and described in the literature.

Preferred examples of AMPA receptor antagonising compounds include those described in e.g. EP 451626, EP 432648, EP 503349, EP 522494, WO 93/05043, EP 633262, WO 94/26747, EP 629615, EP 667340, WO 96/08494, WO 96/08495, WO 96/08494 and WO 98/14447, and the quinoxaline- or quinoxalinedione derivatives, in particular 2,3-dihydroxy-6-nitro-7-sulphamoyl-benzo-(f)-quinoxaline (NBQX), and 6,7-dinitroquinoxaline-2,3-dione or 6-cyano-7-nitroquinoxaline-2,3-dione.

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 100 mg, are suitable for therapeutic treatments.

The active ingredient may be administered in one or several doses per day. A satisfactory result can, in certain instances, be obtained at a dosage as low as 0.1 $\mu$g/kg i.v. and 1 $\mu$g/kg p.o. The upper limit of the dosage range is presently considered to be about 10 mg/kg i.v. and 100 mg/kg p.o. Preferred ranges are from about 0.1 $\mu$g/kg to about 10 mg/kg/day i.v., and from about 1 $\mu$g/kg to about 100 mg/kg/day p.o.

BRIEF DESCRIPTION OF THE DRAWINGS

The present invention is further illustrated by reference to the accompanying drawing, in which.

EXAMPLES

Figure 1:
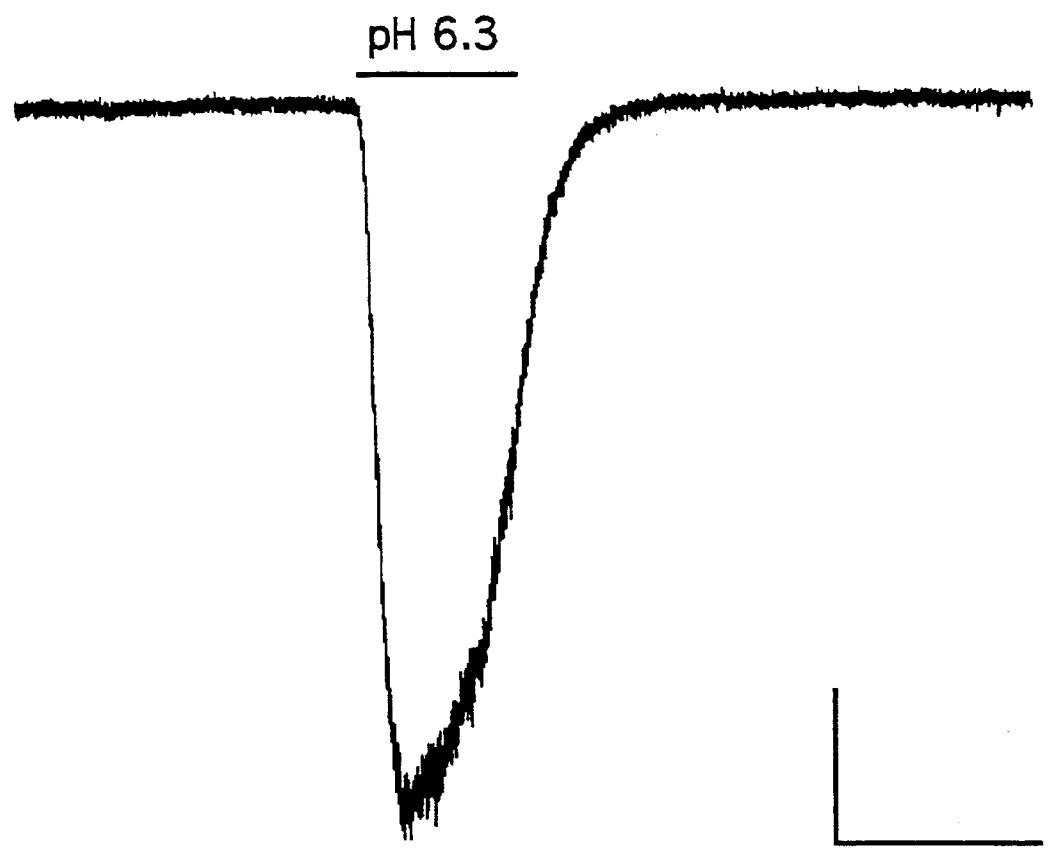
FIG. 1 shows the response to acidic saline recorded from a cultured mouse cortical neuron [A neuron voltage clamped at −60 mV and by means of a flowpipe the extracellular solution surrounding the neuron was changed rapidly from pH 7.4 to pH 6.3 for 750 msec; Scale bars: 200 pA/1 sec.]

The invention is further illustrated with reference to the following examples which are not intended to be in any way limiting to the scope of the invention as claimed.

Example 1

Preparatory Example

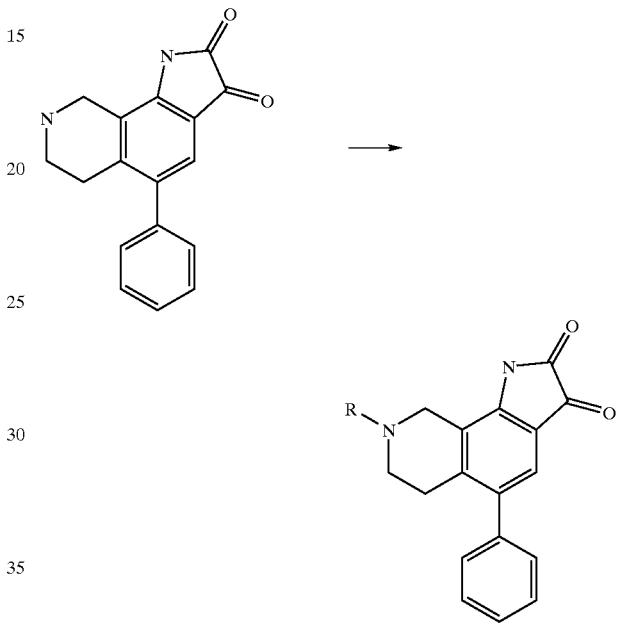

8-methoxycarbonylmethyl-5-phenyl-6.7,8,9-tetrahydro-1H-pyrrolo-[3,2-h]-isoquinoline-2,3-dione (Compound 1A).

A suspension of 5-phenyl-6,7,8,9-tetrahydro-1H-pyrrolo [3,2-h]-isoquinoline-2,3-dione (0.278 g), methylbromoacetat (107.35 μl) and potassium carbonate (0.138 g) in methanol (20 ml) was stirred at room temperature for 24 hours. The suspension was partly evaporated and water (20 ml) was added. This afforded a solid precipitate which was collected by filtration.

In exactly the same manner the following compounds were obtained:

8-(2-propynyl)-5-phenyl-6,7,8,9-tetrahydro-1H-pyrrolo[3, 2-h]-isoquinoline-2,3-dione (Compound 1B) from 5-phenyl-6,7,8,9-tetrahydro-1H-pyrrolo[3,2-h]-isoquinoline-2,3-dione and propargylbromide;
8-cyclopropylmethyl-5-phenyl-6,7,8,9-tetrahydro-1H-pyrrolo[3,2-h]-isoquinoline-2,3-dione (Compound 1C) from 5-phenyl-6,7,8,9-tetrahydro-1H-pyrrolo[3,2-h]-isoquinoline-2,3-dione and cyclopropylbromide; and
8-benzyl-5-phenyl-6,7,8,9-tetrahydro-1H-pyrrolo[3,2-h]-isoquinoline-2,3-dione (Compound 1D) from 5-phenyl-6, 7,8,9-tetrahydro-1H-pyrrolo[3,2-h]-isoquinoline-2,3-dione and benzylbromide.

Example 2

Preparatory Example

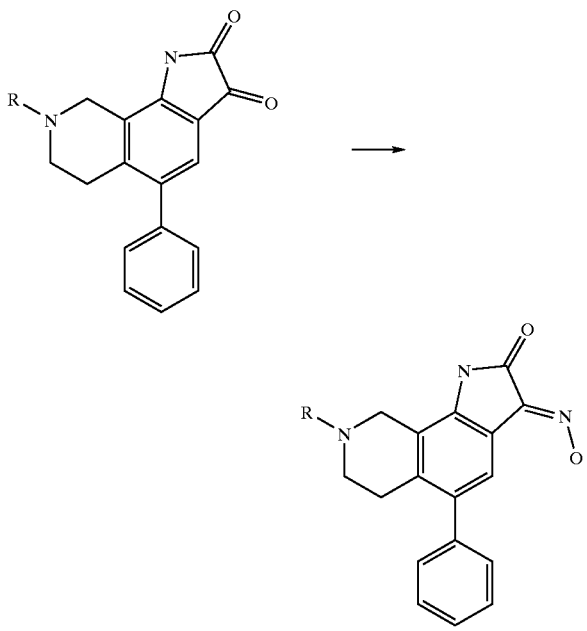

8-methoxycarbonylmethyl-5-phenyl-6,7,8,9-tetrahydro-1H-pyrrolo-[3,2-h]-isoquinoline-2,3-dione-3-oxime (Compound 2A)

8-methoxycarbonylmethyl-5-phenyl-6,7,8,9-tetrahydro-1H-pyrrolo-[3,2-h]-isoquinoline-2,3-dione (0.25 g) and hydroxylamine hydrochloride (76 mg) was added with stirring to hot (50° C.) methanol (25 ml). After 2 hours of stirring the reaction mixture was concentrated by evaporation. At room temperature water (20 ml) was added.

This afforded a solid precipitate of the product as the hydrochloride (90 mg). The free base could be obtained by treatment with carbonate.

M.p. of the free base 165° C. (decomp).

In a similar manner the following compounds were prepared from the corresponding diones:

8-(2-propynyl)-5-phenyl-6,7,8,9-tetrahydro-1H-pyrrolo[3,2-h]-isoquinoline-2,3-dione-3-oxime (Compound 2B)

M.p. 170° C. (decomp.).

8-cyclopropylmethyl-5-phenyl-6,7,8,9-tetrahydro-1H-pyrrolo[3,2-h]-isoquinoline-2,3-dione-3-oxime (Compound 2C)

M.p. 170° C. (decomp.).

8-benzyl-5-phenyl-6,7,8,9-tetrahydro-1H-pyrrolo[3,2-h]-isoquinoline-2,3-dione-3-oxime (Compound 2D)

M.p. 160° C. (decomp.).

8-ethyl-5-phenyl-6-7-8-9-tetrahydro-1-methyl-pyrrolo-[3,2-h]-isoquinoline-2,3-dione-3-methyloxim (Compound 2E).

8-ethyl-5-phenyl-6-7-8-9-tetrahydro-1-methyl-pyrrolo-[3,2-h]-isoquinoline-2,3-dione-3-O-methyloxim (Compound 2F).

Example 3

Biological Activity

This example demonstrates the existence of proton-gated cation channels in cultured mouse cortical neurons, and the effect of Amiloride on these neurons.

The following experiments were performed in voltage—or current clamp using conventional whole cell patch clamp methods [Hamill O P, Marty A, Neher E, Sakmann B and Sigworth F J: Improved patch-clamp techniques for high-resolution current recording from cells and cell-free membrane patches; *Pflügers Arch.* 1981 39 85–100]. The following salt solutions were used (where nothing else stated, the chemicals are available from Sigma): NaCl (140 mM), KCl (4 mM), $CaCl_2$ (2 mM), $MgCl_2$ (1 mM), Sucrose (30 mM; Available from Fluka Chemie, Buchs, Switzerland), HEPES (10 mM, pH 6–7.4). Solutions with pH <6 were buffered with MES (10 mM) in stead of HEPES. Solutions with no added $Ca^{2+}$ contained 3 mM $MgCl_2$. Solutions with no added $Na^+$ contained 140 mM N-methyl-D-glucamine. For voltage clamp experiments, the extracellular solutions were added Tetrodotoxin (0.0003 mM; Available from Alomone Labs, Jerusalem, Israel) and Bicuculline Methiodide (0.005 mM; Available from RBI, MA, USA).

Intracellular solution for voltage clamp experiments: CsCl (120 mM), CsF (20 mM), $MgCl_2$ (2 mM), EGTA (10 mM), HEPES (10 mM; pH=7.2). Intracellular solution for current clamp experiments: KCl (151 mM), $MgCl_2$ (1.8 mM), EGTA (10 mM), HEPES (10 mM, pH=7.2). In all solutions, pH was adjusted with HCl.

Cell Cultures

Mouse neocortical neurons were cultured essentially as described by Drejer et al. (Drejer J, Honoré T and Schousboe A: Excitatory amino acid-induced release of $^3$H-GABA from cultured mouse cerebral cortex inter-neurons; *J. Neurosci.* 1987 7 2910–2916].

Pregnant (9 days) NMRl mice were obtained from Bomholtgaard Breeding and Research Center, Ry, Denmark, and horse serum, N2 supplement and culture media were purchased from Life Technologies (GIBCO), Roskilde, Denmark.

Briefly, the forebrains from the embryonic (E17) NMRl mice were removed under sterile conditions. The tissue was chopped in 0.4 mm cubes and the triturated with trypsin (12.5 μg/ml) and DNAse (2.5 μg/ml), 15 min, 37° C. The cells were suspended at a concentration of $1 \times 10^6$ cells/ml in a slightly modified DMEM which contained horse serum (10% v/v), penicillin (333 U/ml), para-aminobenzoic acid (1 μg/ml), L-glutamine (0.5 mM), insulin (0.08 U/ml) and KCl (23.8 mM). The cell suspension was subsequently inoculated into poly-L-lysine coated 35 mm Petri dishes (2 ml/dish). Glass coverslips (3.5 mm) were placed in the dishes before coating. After 24 hr in culture, the medium was replaced by freshly made medium containing 1% N2 supplement instead of serum.

The cells were kept in culture for 5–14 days at 37° C. (5% $CO_2$/95% $O_2$) before experiments were carried out.

Electronics, Programs and Data Acquisition

The amplifier used was the EPC-9 (HEKA-electronics, Lambrect, Germany) run by a Power Macintosh G3 computer via an ITC-16 interface. Experimental conditions were set with the Pulse-software accompanying the amplifier. Data were low pass filtered and sampled directly to hard-disk at a rate of 3 times the cut-off frequency.

Pipettes and Electrodes

Pipettes were pulled from borosilicate glass (Modulohm, Copenhagen, Denmark) using a horizontal electrode puller (Zeitz-lnstrumente, Augsburg, Germany). The pipette resistances were 1.7–2.4 MΩ in the salt solutions used in these experiments. The pipette electrode was a chloridized silver wire, and the reference was a silverchloride pellet electrode (in Vivo Metric, Healdsburg, USA) fixed to the experimental chamber. The electrodes were zeroed with the open pipette in the bath just prior to sealing.

Experimental Procedure

Coverslips were transferred to a 15 μl experimental chamber mounted on the stage of an inverted microscope (IMT-2, Olympus) supplied with Nomarski optics. Cells were continuously superfused with extracellular saline (pH 7.4) at a rate of 2.5 ml/min. After giga-seal formation (1–5 GΩ, success-rate=90%) the whole cell configuration was attained by suction.

For voltage clamp experiments, the cells were held at a holding voltage of −60 mV and at the start of each experiment the current was continuously measured for at least 30 sec. to ensure a stable leak current. Solutions buffered at pH 5–7.4 were delivered to the chamber through a custom-made gravity-driven flowpipe, the tip of which was placed approximately 50 μm from the cell. Application was triggered when the tubing connected to the flow pipe was compressed by a valve controlled by the Pulse-software. Unless indicated otherwise, acidic solutions were applied for 1 sec. every 45 sec. The concentration of Amiloride when tested and of electrolytes were identical in the chamber and in the flowpipe. Effect of Amiloride was calculated as the current at compound equilibrium divided by the current evoked by the pulse immediately before the compound was included.

For current clamp experiments, a maximum of 50 pA of holding current was injected to ensure a membrane potential between −55 and −65 mV.

The sample interval in all experiments was 310 μsec.

All experiments were performed at room temperature (20–25° C.).

Results

In voltage clamp, rapid shifts of the extracellular saline from pH 7.4 to pH <7.0 invariable triggered inward currents, which desensitised considerably with prolonged activation by pH <~6.8 (An example with pH 6.3 is shown in FIG. 1.

Figure 2:
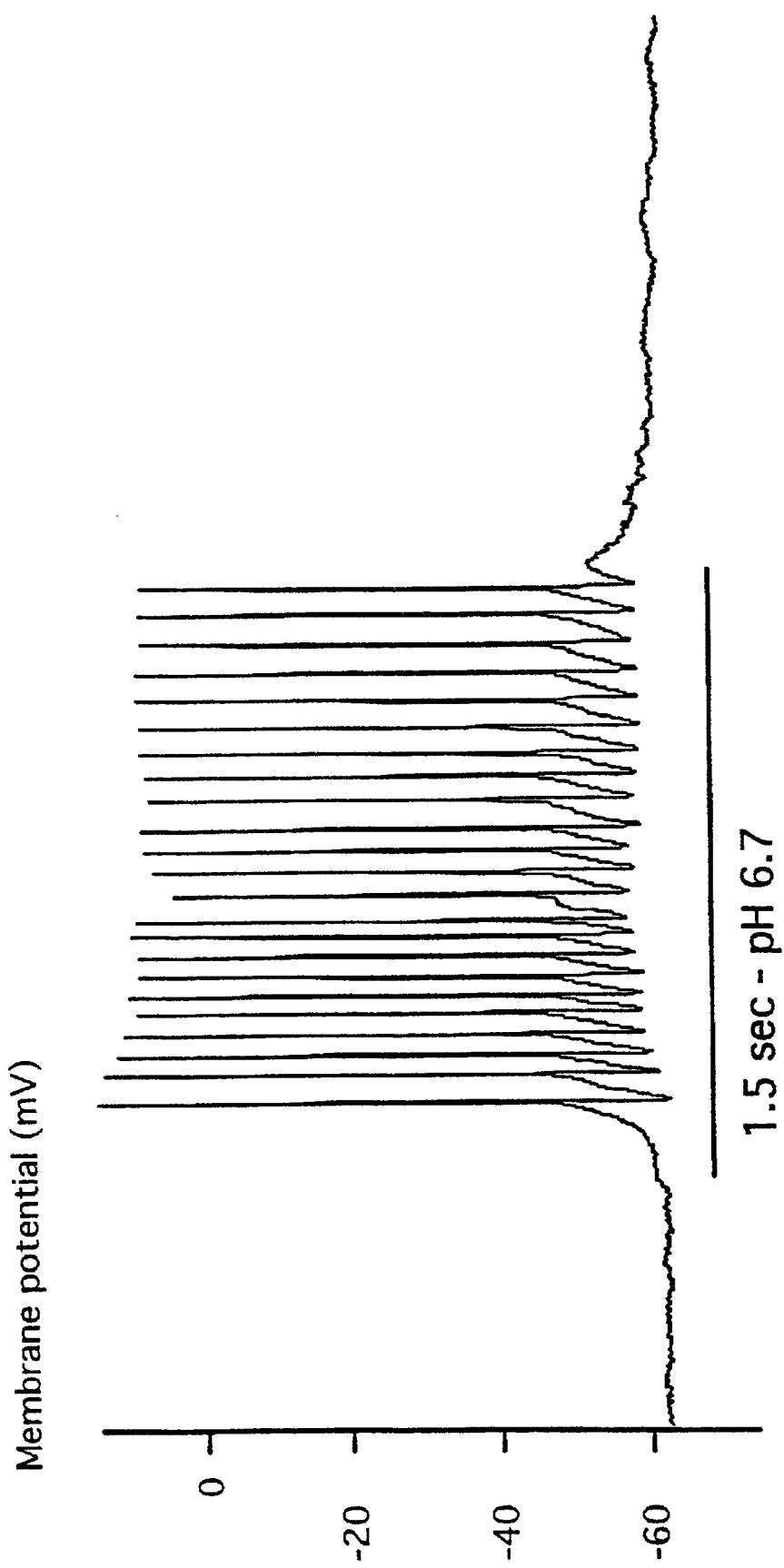
FIG. 2 shows the changes in membrane potential of a cultured mouse cortical neuron induced by acidic saline [Activation of acid-sensing ion channels depolarises neurons and triggers action potentials; A cortical neuron current clamped ($I_n$: 0 pA) and subjected to a 1.5 sec. pulse of saline at pH 6.7; The depolarisation triggered a train of action potentials that lasted for as long as the acidic pulse]

In current clamp pulses of acidic saline depolarised the neurons, and when TTX was omitted from the extracellular saline, trains of action potentials were triggered (see FIG. 2).

Figure 3:
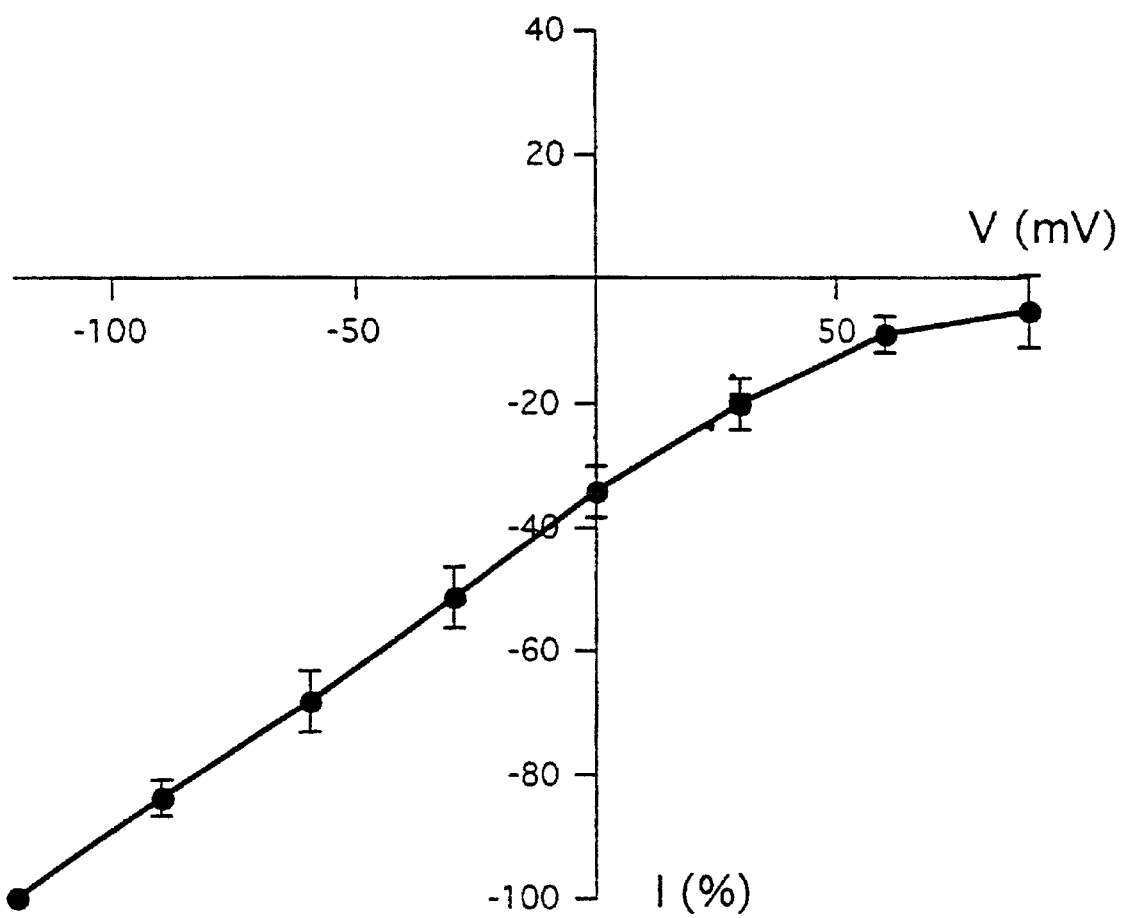
FIG. 3 shows the IV-relation for acid-induced currents in a cultured cortical neuron [In this experiment the extracellular saline contained 140 mM $Na^+$ and 2 mM $Ca^{2+}$; The intracellular solution contained 140 mM $Cs^+$; Neurons were voltage clamped initially at −60 mV; Every 45 sec. the membrane potential was changed (from −120 to +90 mV in 30 mV steps) for 4 sec.; 2.5 sec. after changing the potential, the response was evoked by a 1 sec. pulse of saline at pH 6; In each experiment, the responses are scaled to the response evoked at −120 mV (100%); Data points represent mean ±S.D. (n=8, except Vm=+90 mV, n=3)]

Ion substitution experiments revealed that the currents were carried exclusively by $Na^+$ and were moderately inhibited by extracellular $Ca^{2+}$. The IV-relation for currents triggered by pH 6.5 with physiological extracellular saline and caesium as the major intracellular cation is shown in FIG. 3.

Figure 4:
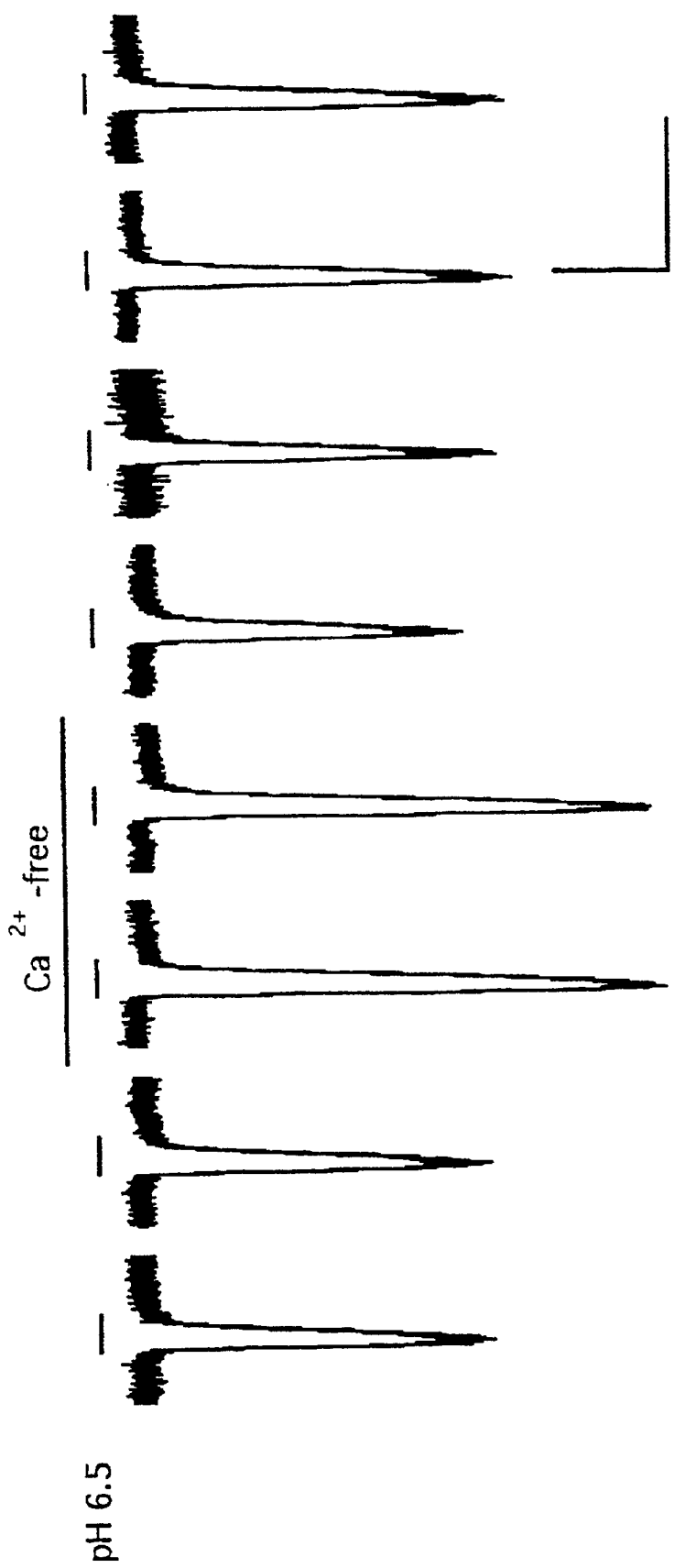
FIG. 4 shows the responses to acid recorded from a cultured mouse cortical neuron in presence/absence of extracellular $Ca^{2+}$ [Proton-gated currents in cortical neurons are moderately inhibited by extracellular $Ca^{2+}$; A neuron was voltage clamped at −60 mV and inward currents were evoked every 45 sec. by 1 sec. applications of saline at pH 6.5 (short horizontal lines); After attainment of responses with a stable amplitude (only two responses shown), the extracellular solutions in the bath (pH 7.4, 2 mM $Ca^{2+}$) and in the flowpipe (pH 6.5, 2 mM $Ca^{2+}$) were changed to similar solutions where $Ca^{2+}$ had been substituted by $Mg^{2+}$; After two responses, solutions were changed back to 2 mM $Ca^{2+}$; Scale bars: 100 pA/5 sec]

When extracellular sodium was substituted by N-methyl-D-glucamine, no inward currents could be measured—even when the $Ca^{2+}$ content was increased from 2 to 10 mM. Substitution of extracellular $Ca^{2+}$ with $Mg^{2+}$, potentiated the responses triggered by pH 6.5 by 39±19% (n=13). An example is shown in FIG. 4.

Figure 5:
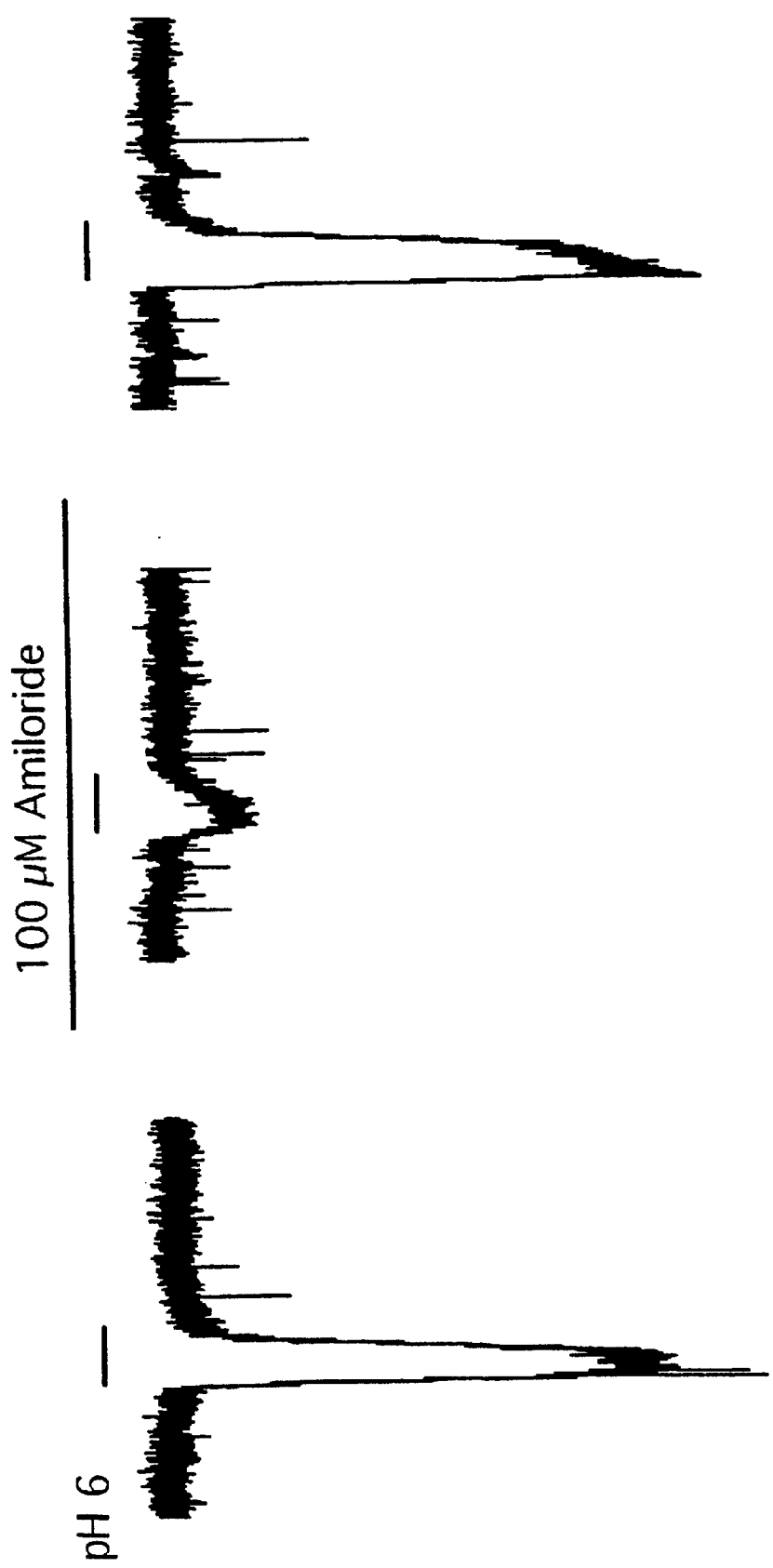
FIG. 5 shows the responses to acid recorded from a cultured mouse cortical neuron in presence/absence of Amiloride [Proton-gated currents in cortical neurons are inhibited by Amiloride; A neuron was voltage clamped at −60 mV and inward currents were evoked every 45 sec. by 1 sec. applications of saline at pH 6 (short horizontal lines); After attainment of responses with a stable amplitude (only one response shown), the extracellular solutions in the bath (pH 7.4) and in the flowpipe (pH 6) were changed to similar solutions containing 100 μM Amiloride; After obtaining responses of a new stable amplitude (only one response shown), solutions were changed back to control; Scale bars:100 pA/2 sec.]

The currents were also inhibited by the diuretic Amiloride (see FIG. 5), a characteristic previously described for of cloned proton-gated channels.

Figure 6:
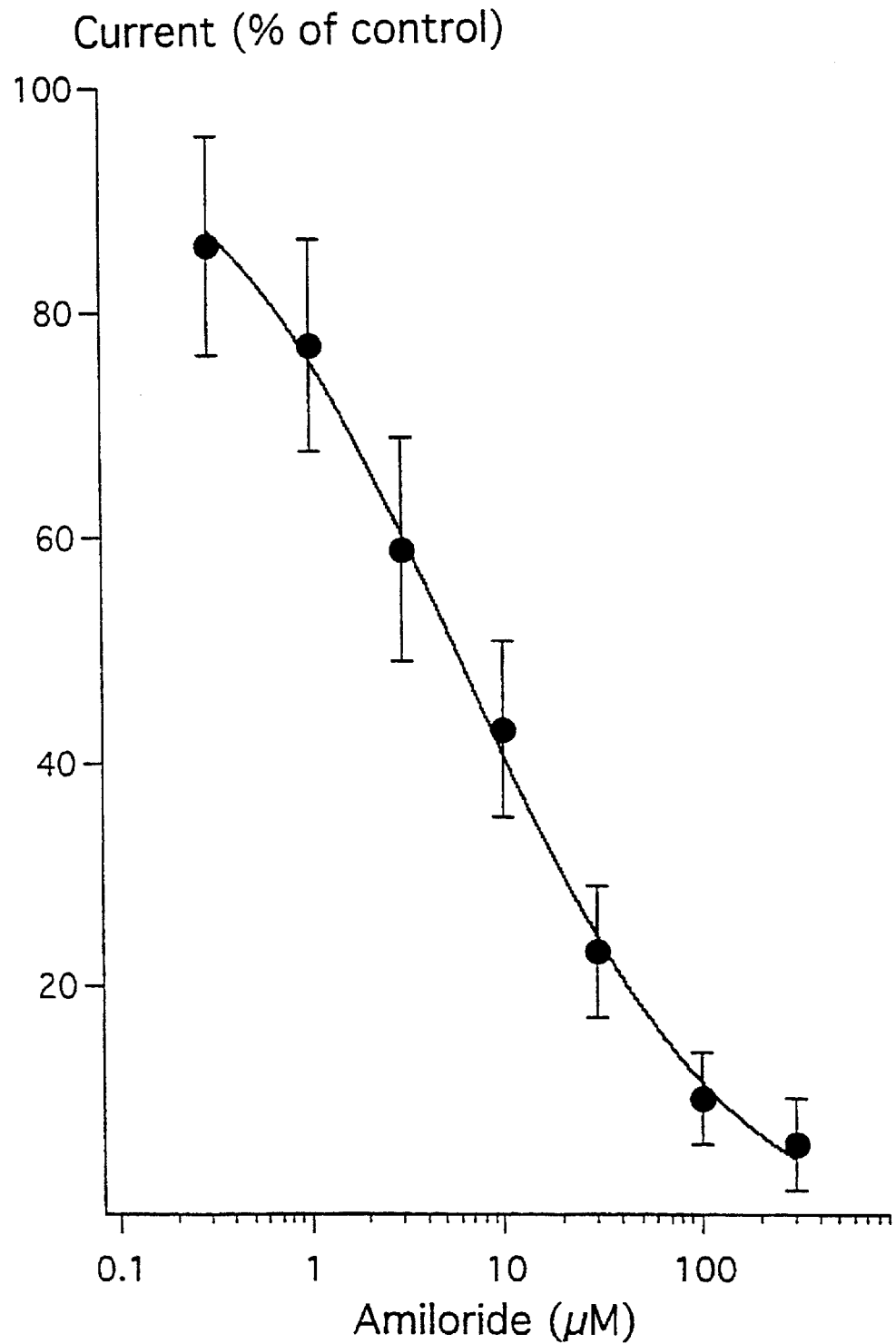
FIG. 6 shows the effect of Amiloride on the current responses recorded from a cultured mouse cortical neuron [Amiloride inhibits proton-gated currents in a concentration dependent manner; The experiments were performed after the protocol depicted in FIG. 5; The data points represent mean±S.D. (n=3–5); The data were fitted (solid curve) to the Hill equation and the calculated parameters were: $IC_{50}$=6.2 μM and $n_H$=0.65]

The $IC_{50}$ for Amiloride in this study was calculated to 6.2 μM (see FIG. 6).

Figure 7:
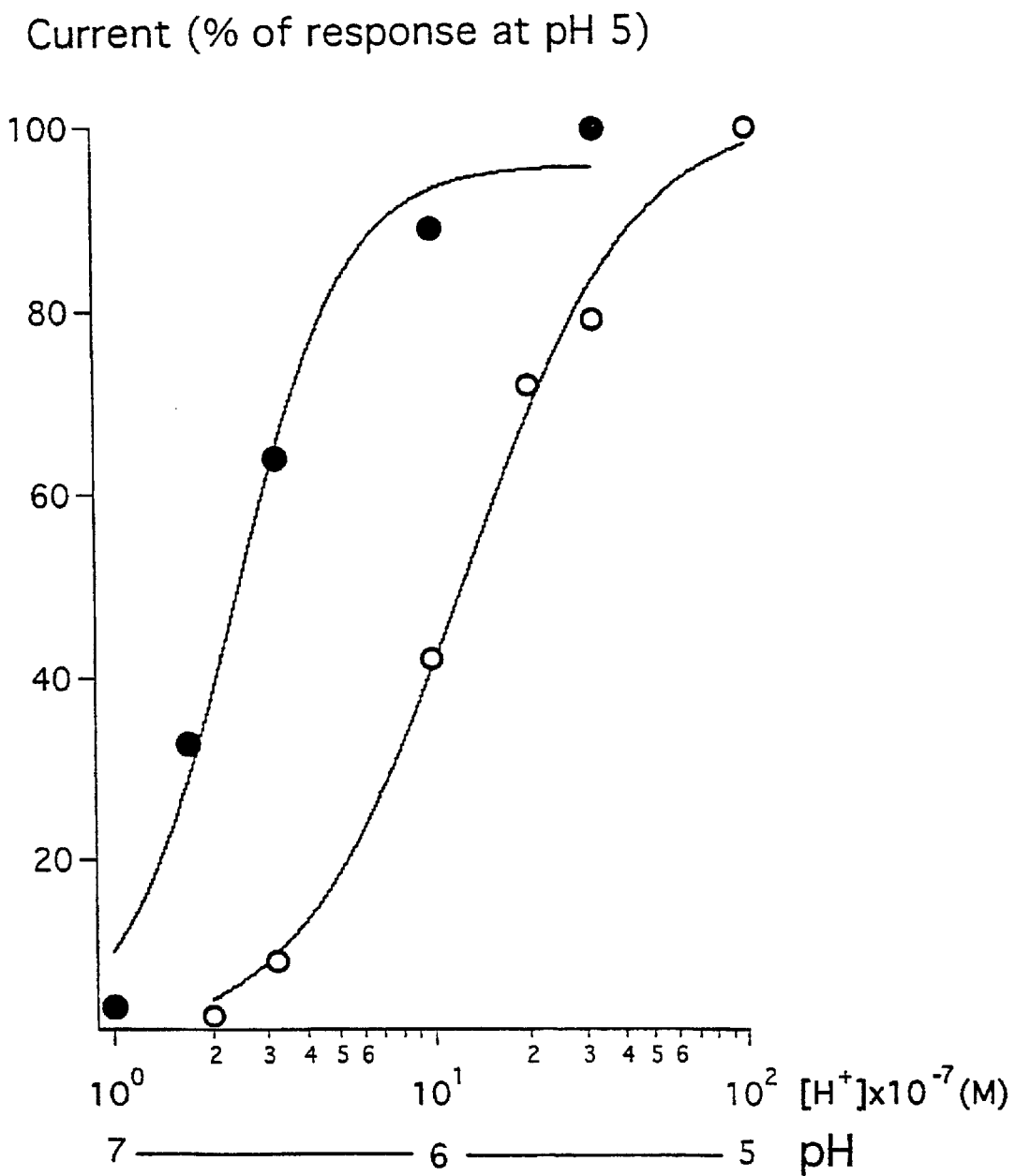
FIG. 7 shows the effect of extracellular pH on cultured mouse cortical neuron [Cultured cortical neurons varies considerably in sensitivity to extracellular acidity; The figure shows concentration-response relationship for two neurons, which were exposed to a series of pulses of saline at different pH; In each experiment, the amplitude of each response was scaled to the amplitude of the response evoked by pH 5 (100%); Data points are fitted to the Hill equation and the parameters calculated for these particular neurons were: Filled symbols: $EC_{50}$=2.4 μM (pH 6.62) and $n_H$=2.4; Open symbols: $EC_{50}$=12.6 μM (pH 5.90) and $n_H$=1.6].

A significant difference among the previously characterised acid sensing ion channels is their variance in proton sensitivity, and the steepness of the concentration response curve. The present work revealed an extreme cell to cell variance in this respect: Full concentration-response experiments were performed on 11 neurons, and the EC50-value for protons varied from pH 6.8 to pH 5.6 with Hill coefficients ranging from 1.17 to 4.46. Two examples are shown in FIG. 7.

Example 4

Biological Activity

In this example the current flux induced by protons over the membrane of a naturally occurring proton-gated cation channel in a HEK293 cell was determined using patch clamp techniques.

Using this technique, the effects of the compounds for use according to the invention was investigated on whole cell currents elicited by a drop in extracellular pH from 7.4 to 6.5.

The following compounds were found to induce inhibition of the proton activated response.

Compounds having $IC_{50}$ below 100 nM:

8-ethyl-5-phenyl-6-7-8-9-tetrahydro-1H-pyrrolo-[3,2-h]-isoquinoline-2,3-dione-3-oxim;
7-ethyl-5-phenyl-6,7,8,9-tetrahydro-1H-pyrrolo-[3,2-f]-isoquinoline-2,3-dione-3-oxim;
7-methyl-5-phenyl-1-6-7-8-tetrahydrobenzo-[2, 1-b:3,4-c]-dipyrrole-2,3-dione-3-oxim;
8-methyl-5-phenyl-6-7-8-9-tetrahydro-1H-pyrrolo-[3,2-h]-isoquinoline-2,3dione-3-oxim;
7-methyl-5-(1-naphthyl)-1-6-7-8-tetrahydrobenzo-[2,1-b:3,4-c]-dipyrrole-2,3-dione-3-oxime;
8-methyl-5-(4-fluorophenyl)-6,7,8,9-tetrahydro-1H-pyrrolo-[3,2-h]-isoquinoline-2,3-dione-3-oxim;
5-(4-chlorophenyl)-8-methyl-6-7-8-9-tetrahydro-1-H-pyrrolo-[3,2-h]-isoquinoline-2,3-dione-3-oxim; and
8-methyl-5-phenyl-6,7,8,9-tetrahydro-1H-pyrrolo-[3,2-h]-isoquinoline-2,3-dione-3-acetyloxim.

Compounds having $IC_{50}$ below 1 μM (of from 100 nM to 1 μM):

7-ethyl-5-phenyl-1-6-7-8-tetrahydrobenzo-[2,1-b:3,4-c]-dipyrrole-2,3-dione-3-oxime;
7-methyl-5-phenyl-1-6-7-8-tetrahydrobenzo-[2,1-b:3,4-c]-dipyrrole-2,3-dione-3-oxime;
8-methyl-5-phenyl-6-7-8-9-tetrahydro-1H-pyrrolo-[3,2-h]-isoquinoline-2,3-dione-3-methyloxim;
5-phenyl-6-7-8-9-tetrahydro-1H-pyrrolo-[3,2-h]-isoquinoline-2,3-dione-3-oxim;
5phenyl-7-methyl-6-7-8-9-tetrahydro-1-methyl-pyrrolo-[3,2-f]-isoquinoline-2,3-dione-3-oxim;
5-(2-naphthyl)-8-methyl-6-7-8-9-tetrahydro-1-H-pyrrolo-[3,2-h]-isoquinoline-2,3-dione-3-oxim;
8-methyl-5-(4-(N,N-dimethylsulfamoyl)-phenyl)-6,7,8,9-tetrahydro-1H-pyrrolo-[3,2-h]-isoquinoline-2,3-dione-3oxime;
8-methyl-5-(3-methoxyphenyl)-6-7-8-9-tetrahydro-1-H-pyrrolo-[3,2-h]-isoquinoline-2,3-dione-3-oxim;
8-methyl-5-phenyl-6-7-8-9-tetrahydro-1-H-pyrrolo-[3,2-h]-isoquinoline-2,3-dione-3-O-2,2-dimethylpropanoyl-oxim;
8-methyl-5-(2-methoxyphenyl)-6,7,8,9-tetrahydro-1-H-pyrrolo-[3,2-h]-isoquinoline-2,3-dione-3-oxim;
8-benzyl-5-phenyl-6-7-8-9-tetrahydro-1H-pyrrolo-[3,2-h]-isoquinoline-2,3-dione-3-oxime;
8-cyclopropylmethyl-5-phenyl-6,7,8,9-tetrahydro-1H-pyrrolo-[3,2-h]-isoquinoline-2,3-dione-3-oxime; and
8-ethyl-5-phenyl-6-7-8-9-tetrahydro-1-methyl-pyrrolo-[3,2-h]-isoquinoline-2,3-dione-3-oxim.

Compounds having $IC_{50}$ below 10 μM (of from 1 μM to 10 μM):

8-methyl-5-(4-nitrophenyl)-6,7,8,9-tetrahydro-1H-pyrrolo-[3,2-h]-isoquinoline-2,3-dione-3-oxim;
5-phenyl-6-7-8-9-tetrahydro-1-H-pyrrolo-[3,2-h]-naphthalene-2,3-dione-3-oxim;
8-methyl-5-(4-toluyl)-6-7-8-9-tetrahydro-1-H-pyrrolo-[3,2-h]-isoquinoline-2,3-dione-3-oxim;
8-methyl-5-(4-methoxyphenyl)-6-7-8-9-tetrahydro-1-H-pyrrolo-[3,2-h]-isoquinoline-2,3-dione-3-oxim;

5-(4-chlorophenyl)-6-7-8-9-tetrahydro-1-H-pyrrolo-[3,2-h]-naphthalene-2,3-dione-3-oxim;

8-methoxycarbonylmethyl-5-phenyl-6,7,8,9-tetrahydro-1H-pyrrolo-[3,2-h]-isoquinoline-2,3-dione-3-oxime;

8-(2-propynyl)-5-phenyl-6,7,8,9-tetrahydro-1H-pyrrolo-[3,2-h]-isoquinoline-2,3-dione-3-oxime; and 8-ethyl-5-phenyl-6-7-8-9-tetrahydro-1-methyl-pyrrolo-[3,2-h]-isoquinoline-2,3-dione-3-O-methyloxim.

What is claimed is:

1. A method of inhibiting a mammalian proton-gated ion channel with an isatin derivative represented by the general Formula I

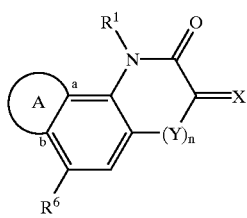
(I)

or a pharmaceutically acceptable salt thereof, wherein $R^1$ represents hydrogen, alkyl, phenyl or benzyl; and X represents oxygen, or a group of the formula $NOR^2$, wherein $R^2$ represents hydrogen, alkyl, acyl, phenyl, or benzyl; and Y represents a group of the formula $N—R^4$, wherein $R^4$ represents hydrogen, hydroxy or alkyl; and n is 0; and $R^6$ represents phenyl, naphthyl, thienyl, or pyridyl all of which groups may be substituted one or more times with halogen, $CF_3$, nitro, amino, cyano, hydroxy, alkyl, alkoxy, phenyl, or a group of the formula —$SO_2NR'R''$, wherein R' and R'' independently of each other represents hydrogen or alkyl; and "A" represents ring holding of six atoms, which ring is fused to the benzo-ring at the positions marked "a" and "b", and formed by one or the following bivalent radicals:

(a) —$NR^{12}$—$CH_2$—$CH_2$—$CH_2$— (b),
(a) —$CH_2$—$NR^2$—$CH_2$—$CH_2$— (b),
(a) —$CH_2$—$CH_2$—$NR^{12}$—$CH_2$— (b),
(a) —$CH_2$—$CH_2$—$CH_2$—$NR^{12}$— (b), wherein $R^{12}$ represents hydrogen, alkyl, alkyl substituted with hydoxy, alkoxy-alkyl, alkoxy-carbonyl-alkyl, alkyl-carbonyl-oxy-alkyl, cycloalkyl, cycloalkyl-alkyl, alkenyl, alkynyl, phenyl or benzyl, which phenyl or benzyl group is optionally substituted with halogen, $CF_3$, nitro, amino, cyano, hydroxy-alkyl, alkoxy, or a group of the formula —$SO_2NR'R''$, wherein R' and R'' independently of each other represents hydrogen or alkyl.

2. The method according to claim 1, wherein the compound is represented by the general Formula II

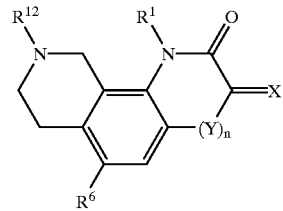
(II)

or a pharmaceutically acceptable salt thereof,
wherein $R^1$, $R^6$, $R^{12}$, X, Y and n have the meanings set forth in claim 1.

3. The method according to claim 1, wherein the compound is represented by the general Formula III

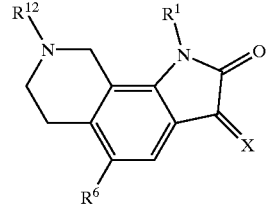
(III)

or a pharmaceutically acceptable salt thereof,
wherein $R^1$, $R^6$, $R^{12}$ and X have the meanings set forth in claim 1.

4. The method according to claim 3, wherein the compound is 8-ethyl-5-phenyl-6-7-8-9-tetrahydro-1H-pyrrolo- [3,2-h]-isoquinoline-2,3-dione-3-oxim;

8-methyl-5-phenyl-6-7-8-9-tetrahydro-1H-pyrrolo- [3,2-h]-isoquinoline-2,3-dione-3-oxim;

8-methyl-5-(4-nitrophenyl)-6,7,8,9-tetrahydro-1H-pyrrolo-[3,2-h]-isoquinoline-2,3-dione-3-oxim;

8-methyl-5-phenyl-6-7-8-9-tetrahydro-1H-pyrrolo-[3,2-h]-isoquinoline-2,3-dione-3-methyloxim;

5-phenyl-6-7-8-9-tetrahydro-1H-pyrrolo-[3,2-h]-isoquinoline-2,3-dione-3-oxim;

8-ethyl-5-phenyl-6-7-8-9-tetrahydro-1-methyl-pyrrolo-[3,2-h]-isoquinoline-2,3-dione-3-oxim;

8-methyl-5-(4-fluorophenyl)-6,7,8,9-tetrahydro-1H-pyrrolo-[3,2-h]-isoquinoline-2,3-dione-3-oxim;

5-(4-chlorophenyl)-8-methyl-6-7-8-9-tetrahydro-1-H-pyrrolo-[3,2-h]-isoquinoline-2,3-dione-3-oxim;

5-(2-naphthyl)-8-methyl-6-7-8-9-tetrahydro-1-H-pyrrolo-[3,2-h]-isoquinoline-2,3-dione-3-oxim;

8-methyl-5-phenyl-6,7,8,9-tetrahydro-1H-pyrrolo-[3,2-h]-isoquinoline-2,3-dione-3-acetyloxim;

8-methyl-5-(4-(N,N-dimethylsulfamoyl)-phenyl)-6,7,8,9-tetrahydro-1H-pyrrolo-[3,2-h]-isoquinoline-2,3-dione-3-oxime;

8-methyl-5-(4-toluyl)-6-7-8-9-tetrahydro-1-H-pyrrolo-[3,2-h]-isoquinoline-2,3-dione-3-oxim;

8-methyl-5-(4-methoxyphenyl)-6-7-8-9-tetrahydro-1-H-pyrrolo-[3,2-h]-isoquinoline-2,3-dione-3-oxim;

8-methyl-5-(3-methoxyphenyl)-6-7-8-9-tetrahydro-1-H-pyrrolo-[3,2-h]-isoquinoline-2,3-dione-3-oxim;

8-methyl-5-phenyl-6-7-8-9-tetrahydro-1-H-pyrrolo-[3,2-h]-isoquinoline-2,3-dione-3-O-2,2-dimethylpropanoyloxim;

8-methyl-5-(2-methoxyphenyl)-6-7-8-9-tetrahydro-1-H-pyrrolo-[3,2-h]-isoquinoline-2,3-dione-3-oxim;

8-benzyl-5-phenyl-6-7-8-9-tetrahydro-1H-pyrrolo-[3,2-h]-isoquinoline-2,3-dione-3-oxim;

8-methoxycarbonylmethyl-5-phenyl-6,7,8,9-tetrahydro-1H-pyrrolo-[3,2-h]-isoquinoline-2,3-dione-3-oxime;

8-(2-propynyl)-5-phenyl-6,7,8,9-tetrahydro-1H-pyrrolo-[3,2-h]-isoquinoline-2,3-dione-3-oxime; or 8-cyclopropylmethyl-5-phenyl-6,7,8,9-tetrahydro-1H-pyrrolo-[3,2-h]-isoquinoline-2,3-dione-3-oxime;

8-ethyl-5-phenyl-6-7-8-9-tetrahydro-1-methyl-pyrrolo[3,2-h]-isoquinoline-2,3-dione-3-oxim;

8-ethyl-5-phenyl-6-7-8-9-tetrahydro-1-methyl-pyrrolo-[3,2-h]-isoquinoline-2,3-dione-3-O-methyloxim;

or a pharmaceutically acceptable salt thereof.

5. The method according to claim 1, wherein the compound is represented by the general Formula IV

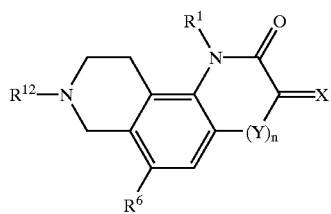

(IV)

or a pharmaceutically acceptable salt thereof,
wherein $R^1$, $R^6$, $R^{12}$, X, Y and n have the meanings set forth in claim 1.

6. The method according to claim 1, wherein the compound is represented by the general Formula V

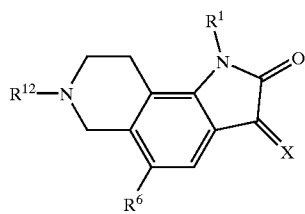

(V)

or a pharmaceutically acceptable salt thereof,
wherein $R^1$, $R^6$, $R^{12}$ and X have the meanings set forth in claim 1.

7. The method according to claim 1, wherein the compound is represented by the general Formula VI

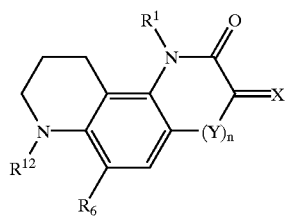

(VI)

or a pharmaceutically acceptable salt thereof,
wherein $R^1$, $R^6$, $R^{12}$, X, Y and n have the meanings set forth in claim 1.

8. The method according to claim 1, wherein the compound is represented by the general Formula VII

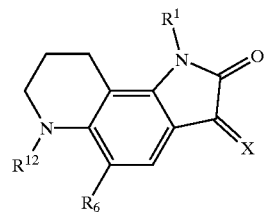

(VII)

or a pharmaceutically acceptable salt thereof,
wherein $R^1$, $R^6$, $R^{12}$ and X have the meanings set forth in claim 1.

9. The method according to claim 8, wherein the compound is 7-ethyl-5--phenyl-6,7,8,9-tetrahydro-1H-pyrrolo-[3,2-f]-isoquinoline-2,3-dione-3-oxim; or 5-phenyl-7-methyl-6-7-8-9-tetrahydro-1-methyl-pyrrolo-[3,2-f]-isoquinoline-2,3-dione-3-oxim;

or a pharmaceutically acceptable salt thereof.

10. A method for the treatment, prevention or alleviation of a disease, disorder or condition in a subject, which disease, disorder or condition is associated with, or mediated by a drop in extracellular pH, which comprises inhibiting cation channels by administering to the subject a pharmaceutically effective amount of an isatin derivative represented by the general Formula I

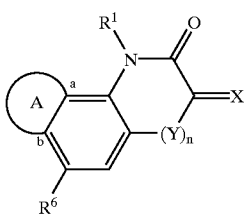

(I)

or a pharmaceutically acceptable salt thereof, wherein
$R^1$ represents hydrogen, alkyl, phenyl or benzyl; and
X represents oxygen, or a group of the formula $NOR^2$, wherein $R^2$ represents hydrogen, alkyl, acyl, phenyl, or benzyl; and
Y represents a group of the formula $N-R^4$, wherein $R^4$ represents hydrogen, hydroxy or alkyl; and
n is 0; and
$R^6$ represents phenyl, naphthyl, thienyl, or pyridyl all of which groups may be substituted one or more times with halogen, $CF_3$, nitro, amino, cyano, hydroxy, alkyl, alkoxy, phenyl, or a group of the formula $-SO_2NR'R''$, wherein R' and R" independently of each other represents hydrogen or alkyl; and
"A" represents ring holding of six atoms, which ring is fused to the benzo-ring at the positions marked "a" and "b", and formed by one or the following bivalent radicals:

(a) $-NR^{12}-CH_2-CH_2-CH_2-$ (b),
(a) $-CH_2-NR^{12}-CH_2-CH_2-$ (b),
(a) $-CH_2-CH_2-NR^2-CH_2-$ (b),
(a) $-CH_2-CH_2-CH_2-NR^{12}-$ (b), wherein
$R^{12}$ represents hydrogen, alkyl, alkyl substituted with hydoxy, alkoxy-alkyl, alkoxy-carbonyl-alkyl, alkyl-carbonyl-oxy-alkyl, cycloalkyl, cycloalkyl-alkyl, alkenyl, alkynyl, phenyl or benzyl, which phenyl or benzyl group is optionally substituted with halogen, $CF_3$, nitro, amino, cyano, hydroxy-alkyl, alkoxy, or a group of the formula —$SO_2NR'R''$, wherein R' and R'' independently of each other represents hydrogen or alkyl.

11. The method according to claim 10, in which the disease or disorder is a diseases associated with reduced blood flow to the brain and other CNS tissue, or associated with instances of a temporary break in blood supply to the brain or to other CNS tissue.

12. The method according to claim 10, in which the disease or disorder is an ischaemic disease, an anoxic episode, an injury to the brain and other parts of the CNS caused by trauma or other injury, a blow to the head, or a spinal injury, a tromboembolic or haemorrhagic stroke, a cerebral vasospasm, hypoglycaemia, cardiac arrest, status epilepticus, perinatal asphyxia, anoxia, cerebral trauma, lathyrism, Alzheimer's disease, and Huntington's disease, cerebral ischaemia or cerebral infarction, ischaemic, hypoxic or anoxic brain damage, spinal cord injury, tissue ischaemia and reperfusion injury in a mammal at risk for such damage.

13. The method according to any of claims 10-12, in which the isatin derivative is an ASIC1-, ASIC1A-, ASIC1B-, ASIC2-, ASIC2A-, ASIC2B-, ASIC3-, or ASTC-β- inhibiting compound.

14. The method according to claim 13, which method further comprises rises simultaneous administration of the isatin derivative and a pharmaceutically effective amount of an AMPA receptor antagonist.

15. The method according to claim 14, wherein the AMPA receptor antagonising compound is 2,3-dihydroxy-6-nitro-7-sulphamoyl-benzo-(f)-quinoxaline (NBQX);

6,7-dinitroquinoxaline-2,3-dione; or 6-cyano-7-nitroquinoxaline-2,3-dione;

or a pharmaceutically acceptable salt thereof.

16. The method of claim 10, wherein the subject is a human being.

\* \* \* \* \*